(12) United States Patent
Anderson (10) Patent No.: US 12,279,945 B2
(45) Date of Patent: Apr. 22, 2025

(54) DYNAMIC LIGAMENT REPAIR DEVICE

(71) Applicant: INS Ortho, Inc., Providence, RI (US)

(72) Inventor: Christian N. Anderson, Nashville, TN (US)

(73) Assignee: INS ORTHO, INC., Providence, RI (US)

( * ) Notice: Subject to any disclaimer, the term of this patent is extended or adjusted under 35 U.S.C. 154(b) by 203 days.

(21) Appl. No.: 17/516,614

(22) Filed: Nov. 1, 2021

(65) Prior Publication Data
US 2022/0168092 A1 Jun. 2, 2022

Related U.S. Application Data

(60) Provisional application No. 63/108,169, filed on Oct. 30, 2020.

(51) Int. Cl.
*A61B 17/04* (2006.01)
*A61F 2/08* (2006.01)

(52) U.S. Cl.
CPC ........ *A61F 2/0811* (2013.01); *A61B 17/0401* (2013.01); *A61B 2017/0404* (2013.01); *A61B 2017/044* (2013.01); *A61B 2017/0458* (2013.01); *A61B 2017/0462* (2013.01); *A61B 2017/0464* (2013.01);
(Continued)

(58) Field of Classification Search
CPC ...... A61B 2017/044; A61B 2017/0404; A61B 2017/0458; A61B 2017/0462; A61B 2017/0464
See application file for complete search history.

(56) References Cited

U.S. PATENT DOCUMENTS 585,564 A 6/1897 Freeman
1,306,369 A 6/1919 Bell
(Continued)

FOREIGN PATENT DOCUMENTS

CA 2846244 C 4/2018
EP 1108401 A1 6/2001
(Continued)

OTHER PUBLICATIONS

Andrews, James R., "BTB ACL Reconstruction: with the ToggleLoc Fixation Device with ZipLoop Technology," Zimmer Biomet, 2017.
(Continued)

*Primary Examiner* — Alexander J Orkin
(74) *Attorney, Agent, or Firm* — Holland & Knight LLP; Matthew C. Cox (57) ABSTRACT

A dynamic ligament repair device includes a suture, a femoral side suture anchor and a threaded screw or housing implant. The screw is configured for placement in the tibia, or alternatively in the femur. A spring is housed inside an axial bore in the threaded screw. In some embodiments, the spring is a compression spring. A moveable spring button is positioned inside the axial bore adjacent a distal end of the spring. The spring button engages the spring directly in some embodiments. In alternative embodiments, an intermediate structure such as a spacer is positioned between the spring button and the spring. The suture extends between the spring button and the suture anchor. When the joint flexes or extends, the spring button travels inside the axial bore and dynamically compresses or relaxes the spring.

19 Claims, 7 Drawing Sheets

(52) U.S. Cl.
CPC .............. *A61F 2002/0817* (2013.01); *A61F 2002/0852* (2013.01); *A61F 2002/0882* (2013.01)

(56) References Cited

U.S. PATENT DOCUMENTS

| | | | |
|---|---|---|---|
| 1,610,309 A | 12/1926 | Otto | |
| 3,409,014 A * | 11/1968 | Shannon | A61B 10/04 24/129 B |
| 3,675,276 A | 7/1972 | Nuse | |
| 4,291,698 A | 9/1981 | Fuchs et al. | |
| 4,773,910 A | 9/1988 | Chen et al. | |
| 4,823,794 A | 4/1989 | Pierce | |
| 4,896,366 A | 1/1990 | Oxman | |
| 5,306,301 A | 4/1994 | Graf et al. | |
| 5,356,412 A * | 10/1994 | Golds | A61B 17/1327 606/151 |
| D359,229 S | 6/1995 | Jules | |
| 5,507,812 A * | 4/1996 | Moore | A61F 2/08 623/13.13 |
| 5,527,341 A | 6/1996 | Gogolewski et al. | |
| 5,645,588 A | 7/1997 | Graf et al. | |
| 5,702,422 A | 12/1997 | Stone | |
| 5,769,894 A | 6/1998 | Ferragamo | |
| 6,066,160 A | 5/2000 | Colvin et al. | |
| 6,099,568 A | 8/2000 | Simonian et al. | |
| 6,517,578 B2 | 2/2003 | Hein | |
| 6,660,023 B2 | 12/2003 | Mcdevitt et al. | |
| 6,666,877 B2 * | 12/2003 | Morgan | D04C 1/12 606/232 |
| 6,716,234 B2 | 4/2004 | Donald et al. | |
| 7,217,279 B2 | 5/2007 | Reese | |
| 7,235,091 B2 | 6/2007 | Thornes | |
| 7,329,271 B2 | 2/2008 | Koyfman et al. | |
| 7,390,332 B2 | 6/2008 | Selvitelli et al. | |
| D576,867 S | 9/2008 | Kretz | |
| 7,530,999 B2 | 5/2009 | Clark et al. | |
| 7,594,922 B1 | 9/2009 | Marlowe et al. | |
| 7,601,165 B2 | 10/2009 | Stone | |
| 7,708,759 B2 * | 5/2010 | Lubbers | A61F 2/0811 606/232 |
| 7,717,929 B2 | 5/2010 | Fallman et al. | |
| 7,776,039 B2 | 8/2010 | Bernstein et al. | |
| 7,862,584 B2 | 1/2011 | Lyons et al. | |
| 7,875,058 B2 * | 1/2011 | Holmes, Jr. | A61B 17/842 606/232 |
| 7,892,256 B2 | 2/2011 | Grafton et al. | |
| 7,905,903 B2 | 3/2011 | Stone et al. | |
| 8,109,968 B2 | 2/2012 | Ashley et al. | |
| 8,118,836 B2 | 2/2012 | Denham et al. | |
| 8,128,658 B2 | 3/2012 | Kaiser et al. | |
| 8,162,997 B2 | 4/2012 | Struhl | |
| 8,231,654 B2 | 7/2012 | Kaiser et al. | |
| 8,231,674 B2 | 7/2012 | Albertorio et al. | |
| 8,298,247 B2 | 10/2012 | Sterrett et al. | |
| 8,348,960 B2 | 1/2013 | Michel et al. | |
| 8,439,976 B2 | 5/2013 | Albertorio et al. | |
| 8,460,379 B2 | 6/2013 | Albertorio et al. | |
| 8,491,632 B2 | 7/2013 | Stone et al. | |
| 8,545,535 B2 | 10/2013 | Hirotsuka et al. | |
| 8,562,645 B2 | 10/2013 | Stone et al. | |
| 8,562,647 B2 | 10/2013 | Kaiser et al. | |
| 8,591,514 B2 | 11/2013 | Sherman | |
| 8,591,578 B2 | 11/2013 | Albertorio et al. | |
| 8,652,172 B2 | 2/2014 | Denham et al. | |
| 8,663,324 B2 | 3/2014 | Schmieding et al. | |
| 8,672,969 B2 * | 3/2014 | Stone | A61B 17/842 606/232 |
| 8,753,375 B2 | 6/2014 | Albertorio | |
| 8,808,374 B2 | 8/2014 | Eggli | |
| 8,821,541 B2 | 9/2014 | Dreyfuss et al. | |
| 8,864,797 B2 | 10/2014 | Justin et al. | |
| 8,876,900 B2 | 11/2014 | Guederian et al. | |
| 8,926,662 B2 | 1/2015 | Perriello et al. | |
| 8,936,621 B2 | 1/2015 | Denham et al. | |
| 8,968,364 B2 | 3/2015 | Berelsman et al. | |
| 9,017,381 B2 | 4/2015 | Kaiser et al. | |
| 9,107,653 B2 | 8/2015 | Sullivan et al. | |
| 9,173,645 B2 | 11/2015 | Overes et al. | |
| 9,179,907 B2 | 11/2015 | Elattrache et al. | |
| 9,192,368 B2 | 11/2015 | Perriello et al. | |
| 9,265,600 B2 | 2/2016 | Niese et al. | |
| 9,289,285 B2 | 3/2016 | Eggli | |
| 9,301,745 B2 | 4/2016 | Dreyfuss | |
| 9,314,234 B2 | 4/2016 | Hirotsuka et al. | |
| 9,326,844 B2 | 5/2016 | Schmieding et al. | |
| 9,345,471 B2 | 5/2016 | Sullivan | |
| 9,381,013 B2 | 7/2016 | Norton | |
| 9,421,007 B2 | 8/2016 | Brady et al. | |
| 9,451,953 B2 | 9/2016 | Sengun et al. | |
| 9,463,011 B2 | 10/2016 | Dreyfuss et al. | |
| 9,463,013 B2 | 10/2016 | Pilgeram et al. | |
| 9,468,433 B2 | 10/2016 | Denham et al. | |
| 9,481,493 B2 | 11/2016 | Vantrease et al. | |
| 9,486,204 B1 | 11/2016 | Ferguson et al. | |
| 9,492,158 B2 | 11/2016 | Stone et al. | |
| 9,498,202 B2 | 11/2016 | Jafari et al. | |
| 9,510,819 B2 | 12/2016 | Stone et al. | |
| 9,615,821 B2 | 4/2017 | Sullivan et al. | |
| 9,622,851 B2 | 4/2017 | Stone et al. | |
| 9,642,610 B2 | 5/2017 | Albertorio et al. | |
| 9,649,189 B2 | 5/2017 | Konicek | |
| 9,693,765 B2 | 7/2017 | Sullivan et al. | |
| 9,700,403 B2 | 7/2017 | Kam et al. | |
| 9,706,985 B2 | 7/2017 | Allen et al. | |
| 9,737,292 B2 | 8/2017 | Sullivan et al. | |
| 9,757,113 B2 | 9/2017 | Pasquali et al. | |
| 9,814,508 B2 | 11/2017 | Volpi et al. | |
| 9,826,969 B2 | 11/2017 | Larsen | |
| 9,888,998 B2 | 2/2018 | Sengun et al. | |
| 9,924,939 B1 * | 3/2018 | Anderson | A61B 17/0487 |
| 9,963,319 B2 | 5/2018 | Ferguson et al. | |
| 10,052,094 B2 | 8/2018 | Spenciner | |
| 10,238,484 B2 | 3/2019 | Albertorio et al. | |
| 10,245,016 B2 | 4/2019 | Zajac et al. | |
| 10,492,774 B2 | 12/2019 | Larsen | |
| 10,646,215 B2 | 5/2020 | Dooney et al. | |
| 2002/0173788 A1 | 11/2002 | Bojarski et al. | |
| 2003/0153948 A1 | 8/2003 | Morrison et al. | |
| 2003/0236555 A1 | 12/2003 | Thornes | |
| 2005/0049635 A1 | 3/2005 | Leiboff | |
| 2005/0065533 A1 | 3/2005 | Magen et al. | |
| 2005/0187577 A1 | 8/2005 | Selvitelli et al. | |
| 2005/0197662 A1 | 9/2005 | Clark et al. | |
| 2006/0282083 A1 * | 12/2006 | Fanton | A61B 17/0401 606/232 |
| 2007/0021781 A1 * | 1/2007 | Jervis | A61B 17/06061 606/232 |
| 2007/0083236 A1 | 4/2007 | Sikora et al. | |
| 2007/0213770 A1 | 9/2007 | Dreyfuss | |
| 2007/0239209 A1 | 10/2007 | Fallman et al. | |
| 2008/0082127 A1 | 4/2008 | Stone et al. | |
| 2008/0255613 A1 | 10/2008 | Kaiser et al. | |
| 2008/0288070 A1 * | 11/2008 | Lo | A61B 17/0401 623/13.13 |
| 2009/0012560 A1 | 1/2009 | Hunter et al. | |
| 2009/0082805 A1 | 3/2009 | Kaiser et al. | |
| 2009/0105754 A1 | 4/2009 | Sethi | |
| 2010/0071833 A1 | 3/2010 | Maiorino | |
| 2010/0160962 A1 | 6/2010 | Dreyfuss et al. | |
| 2010/0256677 A1 | 10/2010 | Albertorio et al. | |
| 2010/0268273 A1 | 10/2010 | Albertorio et al. | |
| 2010/0292792 A1 * | 11/2010 | Stone | A61F 2/0811 623/13.14 |
| 2011/0301708 A1 * | 12/2011 | Stone | A61B 17/0401 606/232 |
| 2012/0046747 A1 | 2/2012 | Justin et al. | |
| 2012/0053630 A1 | 3/2012 | Denham et al. | |
| 2012/0071903 A1 | 3/2012 | Knoell | |
| 2012/0109194 A1 | 5/2012 | Miller et al. | |
| 2012/0116460 A1 | 5/2012 | Gorek | |
| 2012/0123474 A1 | 5/2012 | Zajac et al. | |
| 2012/0130492 A1 * | 5/2012 | Eggli | A61F 2/0811 623/13.14 |

(56) References Cited

U.S. PATENT DOCUMENTS

| | | |
|---|---|---|
| 2012/0150203 A1 | 6/2012 | Brady et al. |
| 2012/0179254 A1 | 7/2012 | Saliman |
| 2012/0290002 A1 | 11/2012 | Astorino |
| 2013/0023928 A1 | 1/2013 | Dreyfuss |
| 2013/0023929 A1 | 1/2013 | Sullivan et al. |
| 2013/0096612 A1 | 4/2013 | Zajac et al. |
| 2013/0110165 A1 | 5/2013 | Burkhart et al. |
| 2013/0116730 A1 | 5/2013 | Denham et al. |
| 2013/0158601 A1 | 6/2013 | Stone et al. |
| 2013/0165972 A1* | 6/2013 | Sullivan .............. A61B 17/0401 606/232 |
| 2013/0168478 A1 | 7/2013 | Holman |
| 2013/0190819 A1 | 7/2013 | Norton |
| 2013/0253647 A1 | 9/2013 | Saliman et al. |
| 2013/0296896 A1 | 11/2013 | Sengun |
| 2013/0296931 A1 | 11/2013 | Sengun |
| 2013/0345749 A1 | 12/2013 | Sullivan et al. |
| 2013/0345750 A1 | 12/2013 | Sullivan |
| 2014/0031864 A1 | 1/2014 | Jafari et al. |
| 2014/0052179 A1 | 2/2014 | Dreyfuss et al. |
| 2014/0114352 A1 | 4/2014 | Allen et al. |
| 2014/0155937 A1 | 6/2014 | Shinde |
| 2014/0250636 A1 | 9/2014 | Vantrease et al. |
| 2014/0257294 A1* | 9/2014 | Gedet .................. A61B 17/842 606/103 |
| 2014/0257346 A1 | 9/2014 | Sengun et al. |
| 2014/0276987 A1 | 9/2014 | Saliman |
| 2014/0277121 A1 | 9/2014 | Pilgeram et al. |
| 2014/0336760 A1 | 11/2014 | Eggli |
| 2014/0350674 A1 | 11/2014 | Stone et al. |
| 2015/0157449 A1 | 6/2015 | Gustafson et al. |
| 2015/0201929 A1 | 7/2015 | Dooney et al. |
| 2015/0297211 A1 | 10/2015 | Sullivan et al. |
| 2015/0297274 A1 | 10/2015 | Dreyfuss et al. |
| 2015/0359530 A1* | 12/2015 | Moore ............... A61B 17/0401 606/232 |
| 2016/0030035 A1 | 2/2016 | Zajac et al. |
| 2016/0157851 A1* | 6/2016 | Spenciner ............. A61F 2/0811 606/232 |
| 2016/0270777 A1 | 9/2016 | Miller et al. |
| 2016/0287243 A1 | 10/2016 | Benedict et al. |
| 2016/0354197 A1* | 12/2016 | Roller ............... A61B 17/0401 |
| 2016/0374662 A1 | 12/2016 | Dreyfuss et al. |
| 2017/0020507 A1* | 1/2017 | Denham .......... A61B 17/06166 |
| 2017/0042556 A1 | 2/2017 | Laprade et al. |
| 2017/0055983 A1 | 3/2017 | Bracy |
| 2017/0128063 A1 | 5/2017 | Jackson |
| 2017/0181739 A1 | 6/2017 | Breslich |
| 2017/0189007 A1 | 7/2017 | Burkhart et al. |
| 2017/0209135 A1 | 7/2017 | Sullivan et al. |
| 2017/0209139 A1 | 7/2017 | Burkhart et al. |
| 2017/0231752 A1 | 8/2017 | Rodriguez et al. |
| 2017/0252033 A1 | 9/2017 | Dreyfuss et al. |
| 2017/0281150 A1 | 10/2017 | Stecco et al. |
| 2017/0333176 A1 | 11/2017 | Stone et al. |
| 2018/0008398 A1 | 1/2018 | Philippot et al. |
| 2018/0064434 A1 | 3/2018 | Jolly et al. |
| 2018/0116785 A1 | 5/2018 | Dreyfuss et al. |
| 2018/0193015 A1 | 7/2018 | Denham et al. |
| 2018/0221133 A1 | 8/2018 | Lund |
| 2018/0221134 A1 | 8/2018 | Sengun et al. |
| 2018/0249998 A1 | 9/2018 | Chavan et al. |
| 2018/0353166 A1 | 12/2018 | Breslich |
| 2019/0099258 A1 | 4/2019 | Armington et al. |
| 2019/0142417 A1 | 5/2019 | Winter |
| 2019/0336190 A1 | 11/2019 | Allard et al. |
| 2019/0365376 A1 | 12/2019 | Stone et al. |
| 2019/0374270 A1 | 12/2019 | Horrell et al. |
| 2020/0015804 A1 | 1/2020 | Bachmaier et al. |
| 2020/0022730 A1 | 1/2020 | Manitzaris et al. |
| 2020/0146667 A1 | 5/2020 | Montross |
| 2020/0197000 A1 | 6/2020 | Dooney et al. |
| 2020/0268372 A1 | 8/2020 | Fallin et al. |
| 2021/0068806 A1 | 3/2021 | Niver et al. |
| 2021/0068809 A1 | 3/2021 | Federspiel et al. |
| 2021/0093316 A1 | 4/2021 | Gustafson |
| 2021/0128138 A1 | 5/2021 | Bettenga |

FOREIGN PATENT DOCUMENTS

| | | |
|---|---|---|
| EP | 2455002 A1 | 5/2012 |
| EP | 2462876 A2 | 6/2012 |
| EP | 2572648 A1 | 3/2013 |
| EP | 2581047 A1 | 4/2013 |
| EP | 2724673 A1 | 4/2014 |
| EP | 2777513 A1 | 9/2014 |
| EP | 2662032 B1 | 10/2015 |
| EP | 2263608 B1 | 9/2016 |
| JP | H06114067 A | 4/1994 |
| JP | 2005237966 A | 9/2005 |
| JP | 2010504828 A | 2/2010 |
| JP | 2010179102 A | 8/2010 |
| JP | 2013233434 A | 11/2013 |
| KR | 20130092425 A | 8/2013 |
| KR | 101872802 B | 6/2018 |
| WO | 2016076977 A1 | 5/2016 |
| WO | 2016149283 A1 | 9/2016 |
| WO | 2020047431 A3 | 4/2020 |

OTHER PUBLICATIONS

Arthrex, "ACL Reconstruction with ACL TightRope," 2015.
Arthrex, "Arthroscopic Stabilization of Acute Acromioclavicular Joint Dislocation using the TightRope System," 2010.
Arthrex, "TightRope Attachable Button System," 2018.
Conmed, "GraftMax Button: Adjustable Cortical Fixation Device," 2015.
Depuy Synthes, "Rigidloop Adjustable Cortical System: Quick Surgical Technique Guide," Nov. 2014.
Dunamis Medical, LLC, "FLIPTight CL Femoral Fixation Device," 2017.
Hartzell, Jeffrey, et al., "JuggerKnotless Soft Anchor for Labral Repair," Zimmer Biomet, 2015.
Hospital Innovations, "Pullup Adjustable loop suspensory fixation," at least as early as Sep. 2020.
Lawhorn, Keith, "MaxFire Marxmen Mensical Repair Device," Biomet, 2014.
Mathys European Orthopaedics, "Ligamys—Healing of the ruptured anterior cruciate ligament".
Mathys European Orthopaedics, "Ligamys: Preservation of the freshly ruptured anterior cruciate ligament," Apr. 2017.
Parcus Medical, LLC, "GFS Ultimate Product Family," at least as early as Mar. 2017.
Parcus Medical, LLC, "GFS Ultimate: Graft Fixation System," at least as early as Mar. 2017.
PCT Application No. PCT/US2018/041059 International Search Report and Written Opinion dated Jan. 4, 2019.
PCT Application No. PCT/US2018/041116 International Search Report and Written Opinion dated Oct. 17, 2018.
PCT Application No. PCT/US2019/048675 International Search Report and Written Opinion dated Dec. 12, 2019.
PCT Application No. PCT/US2021/057627 International Search Report and Written Opinion dated Feb. 24, 2022.
Rosenberg, Thomas D., "ACL reconstruction with the Acufex Director Drill Guide and Endobutton CL Fixation System," Smith & Nephew, 2005.
Smith & Nephew, "Ultrabutton: Adjustable Fixation Device," Feb. 2016.
Stryker, "ProCinch with IntelliBraid Technology, Reference Guide," Dec. 2015.
Stryker, "VersiTomic G-Lok," Feb. 2011.
Tulpar Medical Solutions, "Ext Liftfix Button ACL/PCL: Adjustable Fixation Implant".

* cited by examiner

DYNAMIC LIGAMENT REPAIR DEVICE

CROSS-REFERENCE TO RELATED APPLICATION

This application is a non-provisional of and claims priority to and benefit of U.S. Provisional Patent Application No. 63/108,169 titled "Dynamic Ligament Repair Device" all of which is incorporated by reference herein.

TECHNICAL FIELD

The present invention, described herein, relates generally to devices and methods for orthopedic surgery, and more particularly to devices and methods for repairing ligaments in humans and animals, such as but not limited to the anterior cruciate ligament (ACL) in a human knee.

BACKGROUND

The ACL is not an isometric ligament, and it does not maintain the same length throughout the range of motion of flexion and extension of the knee. Conventional static ACL repair devices tensioned in knee flexion may prevent a patient from being able to fully extend the knee, resulting in a locked joint whereby full extension is uncomfortable or even unattainable. Such outcomes from conventional static ACL repair are generally undesirable, as they inhibit a full range of motion following a ligament repair operation.

To overcome this problem with conventional static ACL repair, others have resorted to tightening the static ACL repair suture construct with the patient's knee in a full extension position. Such procedures offer stability, but as the knee rotates into flexion, the static ACL device may inadvertently loosen because the static suture has a fixed length (but the ACL doesn't maintain a constant length across the full range of motion). As a result, some static ACL repair devices do not serve the intended purpose at higher knee flexion angles. This can cause forces to be exerted on the repaired ACL tissue as opposed to the repair suture construct. Such configurations can lead to the ACL suture ripping from the tissue or causing the repaired tissue to rip away from the bone on the femoral or tibial side. Conventional ACL repair devices also do not promote adequate biological healing because the stresses associated with motion are passed through the ligament instead of being isolated through a suture device.

In summary, conventional suture-based static ACL repair devices when tightened in a flexion position inhibit a full range of extension motion, and when tightened in full extension do not maintain adequate tension across a flexion range of motion.

What is needed then are improvements to ligament repair devices to provide a suitable tension on the ligament across a range of motion to allow proper healing and rehabilitation following a repair operation.

BRIEF SUMMARY

The present disclosure relates to a dynamic ligament repair device and associated methods for re-attaching a torn or separated ligament to bone on the femoral wall and to facilitate natural healing.

One objective of the present disclosure is to provide a dynamic ACL repair device that maintains tension on the knee joint across a full range of motion of the knee in flexion and extension and isolates stress on a suture construct as opposed to the ligament undergoing the repair.

Another objective of the present disclosure is to provide a dynamic ligament repair device including a suture construct with a fixed loop, an adjustable loop, first and second self-cinching sleeves, a screw or housing defining a hollow interior bore, and a compression spring disposed inside the bore, wherein the spring is configured to dynamically maintain tension on the suture construct across a range of motion of the patient's joint.

Another objective of the present disclosure is to provide a method of repairing a ligament, comprising the steps of (a) inserting a threaded housing into bone; (b) passing a suture construct through the housing; (c) positioning a compression spring inside the housing; (d) partially compressing the spring to pre-load the spring; and (e) tightening the suture construct to provide tension against the partially compressed spring. In some embodiments, step (e) includes tightening via one or more self-cinching sleeves disposed on the suture construct. In some embodiments, the method further includes passing a suture stitched to a ligament through a drill tunnel opposite the housing and securing the suture to a suture anchor. In some embodiments, the suture anchor used to secure the ligament suture is the same anchor used to secure the suture construct inserted through the housing for the dynamic ligament repair.

Numerous other objectives, advantages and features of the present disclosure are presented herein and in the accompanying Figures.

DETAILED DESCRIPTION

Figure 1:
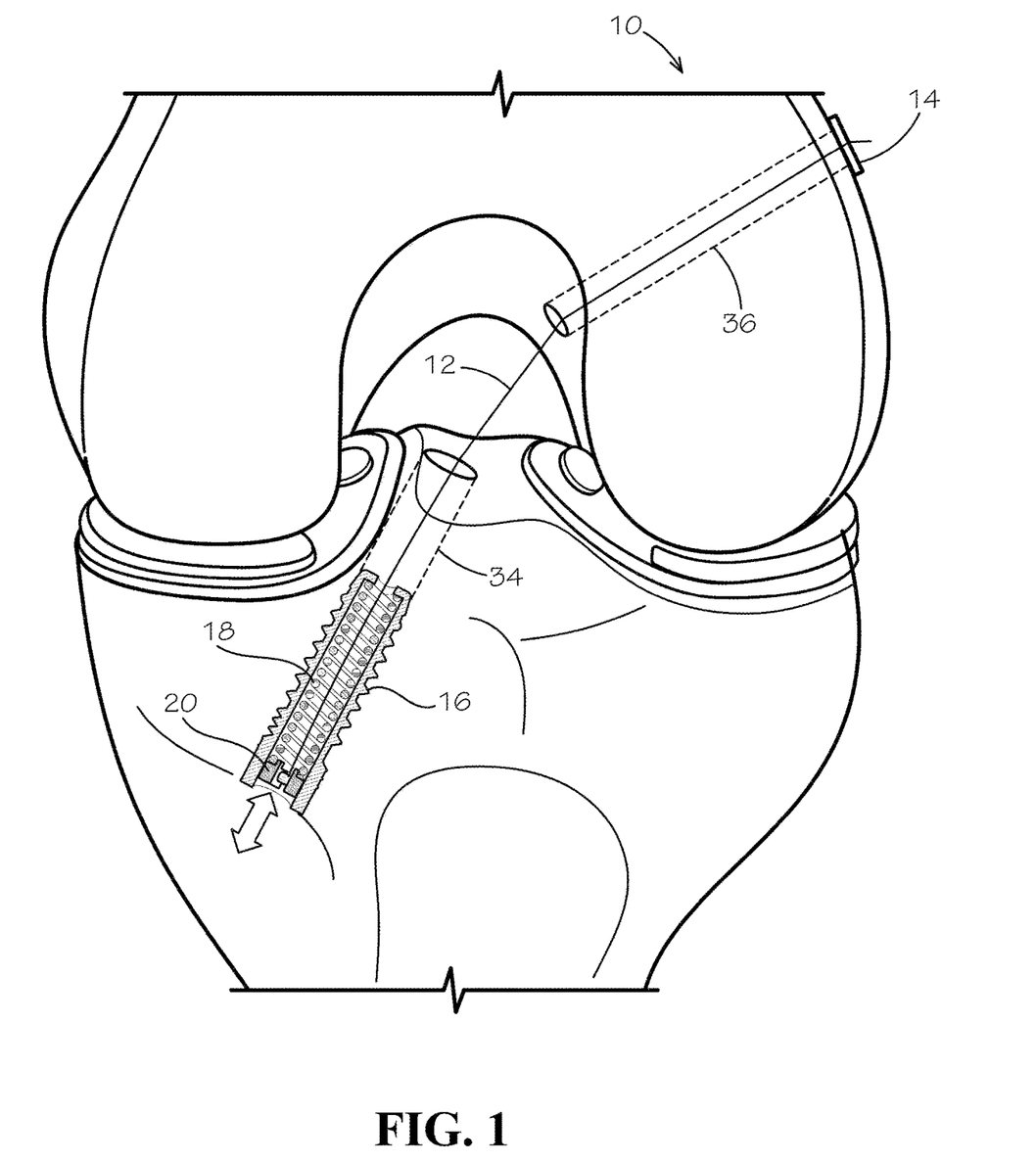
FIG. 1 illustrates a perspective view of an embodiment of a dynamic ligament repair device in accordance with the present disclosure.

The present disclosure relates to devices and methods for dynamic ligament repair. An embodiment of a dynamic ligament repair device 10 is shown in FIG. 1. The device includes a suture 12, a femoral side suture anchor 14 and a threaded screw or housing implant 16. A spring 18 is housed inside an axial bore in the threaded screw 16. A moveable spring button 20 is positioned inside the axial bore adjacent the distal end of the spring 16. The suture 12 extends between the spring button 20 and the suture anchor 14.

Screw 16 has a threaded exterior surface and may be installed into a hole drilled into the bone on the tibia using a driver. Although the screw 16 is shown installed in the tibia in FIG. 1, in reverse configurations the screw 16 may be installed in the femur and the suture anchor 14 positioned on the tibia. In further embodiments, suture anchor 14 includes a second screw assembly including a second screw, a second spring and a second button, and a first screw assembly is disposed in the femur and the second screw assembly is disposed in the tibia, thereby forming a double spring configuration.

As shown in FIG. 1, the dynamic ligament repair device 10 is configured to allow the suture 12 to remain in tension between the suture anchor 14 and the moveable spring button 20 across an entire range of flexion and extension motion of the joint.

During use, spring button 20 may travel inside the axial bore inside screw 16, thereby pulling against and compressing spring 18 when tension is applied to the suture 12, and also allowing spring 18 to expand when tension on suture 12 is relaxed. When the tension is relaxed, the spring 18 will push the spring button away from the joint to maintain tension on suture 12 across the full range of motion. As such, the device 10 provides a dynamic suture-based device for isolating stress while providing repair to ligaments such as the ACL. Although not illustrated in FIG. 1, an ACL undergoing a repair operation may be sutured with a conventional ligament suture that is then passed through a femoral tunnel along with suture 12. The ligament suture may also be secured on the suture anchor 14 to pull the ACL tight against the femur for repair.

The spring-based tension along suture 12 provides a posterior load to the knee in some embodiments. This serves to counteract the anterior force during extension to keep the ACL in a more relaxed state. The spring-based device 10 is able to absorb forces of the natural movement of the knee and to keep those forces off the ACL during rehabilitation and biological healing.

Figure 2:
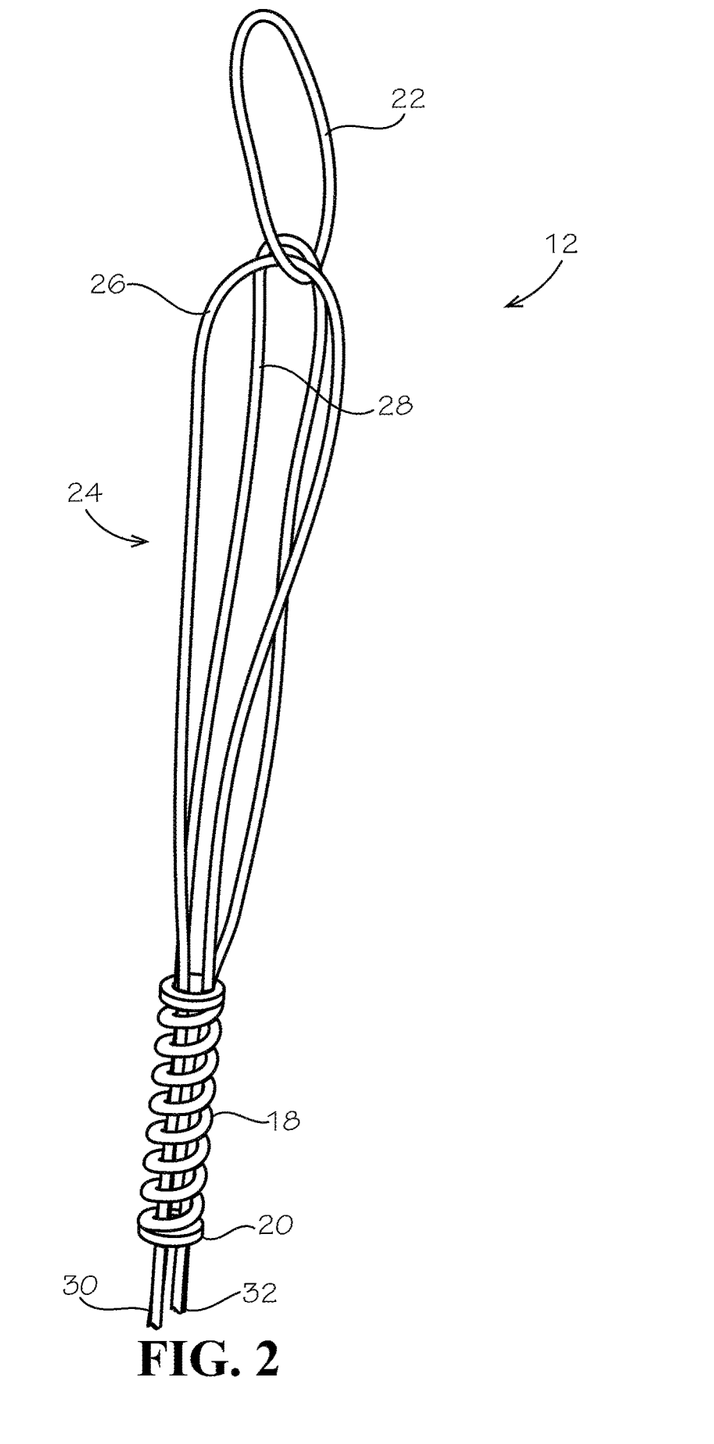
FIG. 2 illustrates a perspective view of an embodiment of a suture construct and spring assembly for use with a dynamic ligament repair device in accordance with the present disclosure.

Referring to FIG. 2, an example of a suture construct 12 for a dynamic ligament repair device 10 is illustrated. Suture 12 includes a pulley loop 22 and a main loop 24. Main loop 24 includes a first strand 26 and a second strand 28. In some embodiments, pulley loop 22 is a fixed loop and main loop 24 is an adjustable loop. A first tag end 30 and a second tag end 32 hang from main loop 24 for selectively tightening the adjustable main loop 24 by shortening first and second strands 26, 28. As shown in FIG. 2, a spring 18 is installed on main loop 24. During use, pulley loop 22 may be pulled through a femoral tunnel 36 using a passing suture. Once pulled through the femoral tunnel 36 to the lateral cortex, the suture anchor 14 may be secured to the pulley loop 22 using any suitable knot such as a girth hitch. In other embodiments, a suture anchor may be secured to pulley loop 22 prior to passage of the pulley loop 22 up through the femoral tunnel 36, wherein the suture anchor is dimensioned to allow passage of the suture anchor through the femoral tunnel 36.

Figure 3:
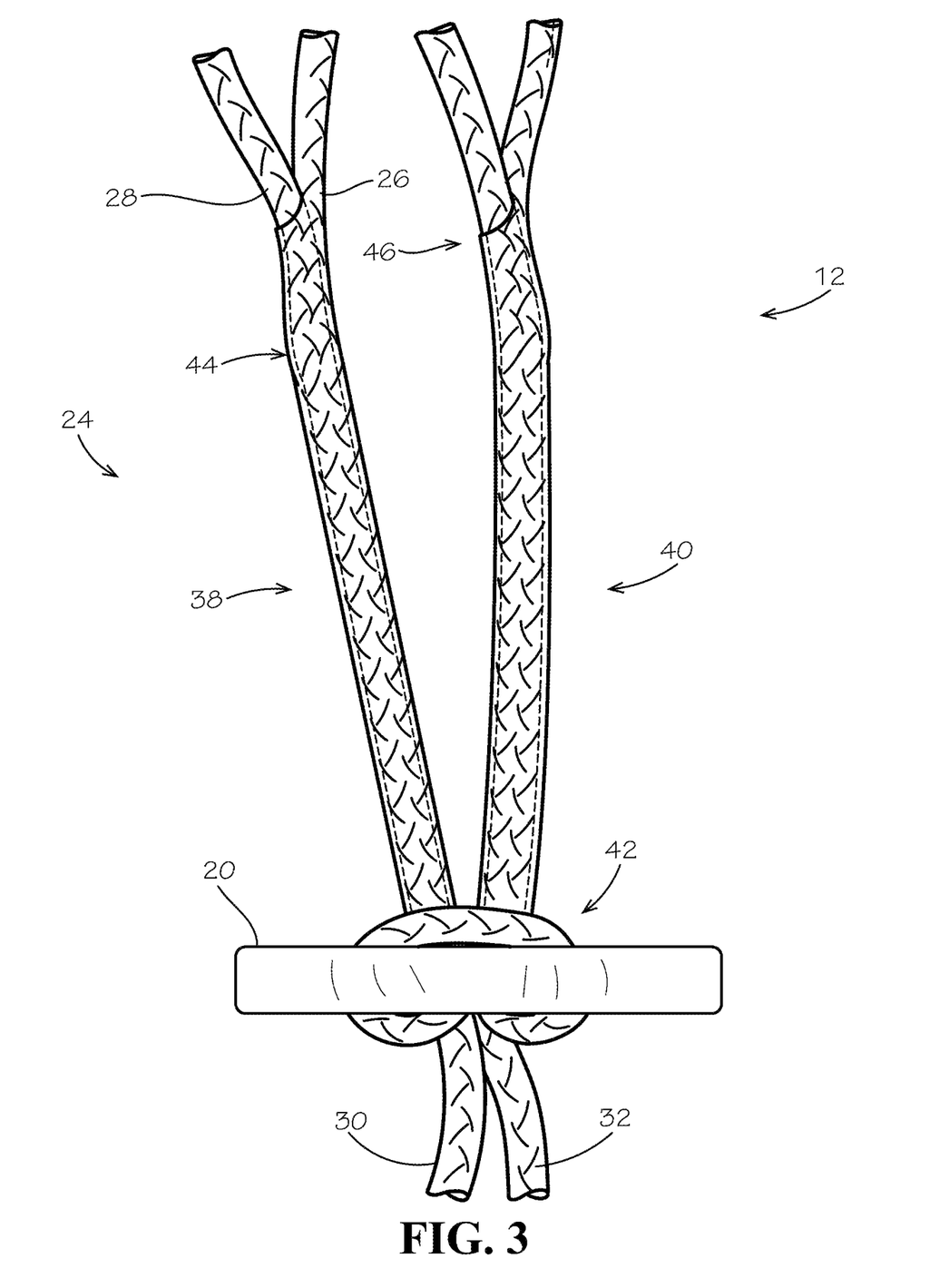
FIG. 3 illustrates a detail perspective view of the suture construct of FIG. 2.
Figure 4:
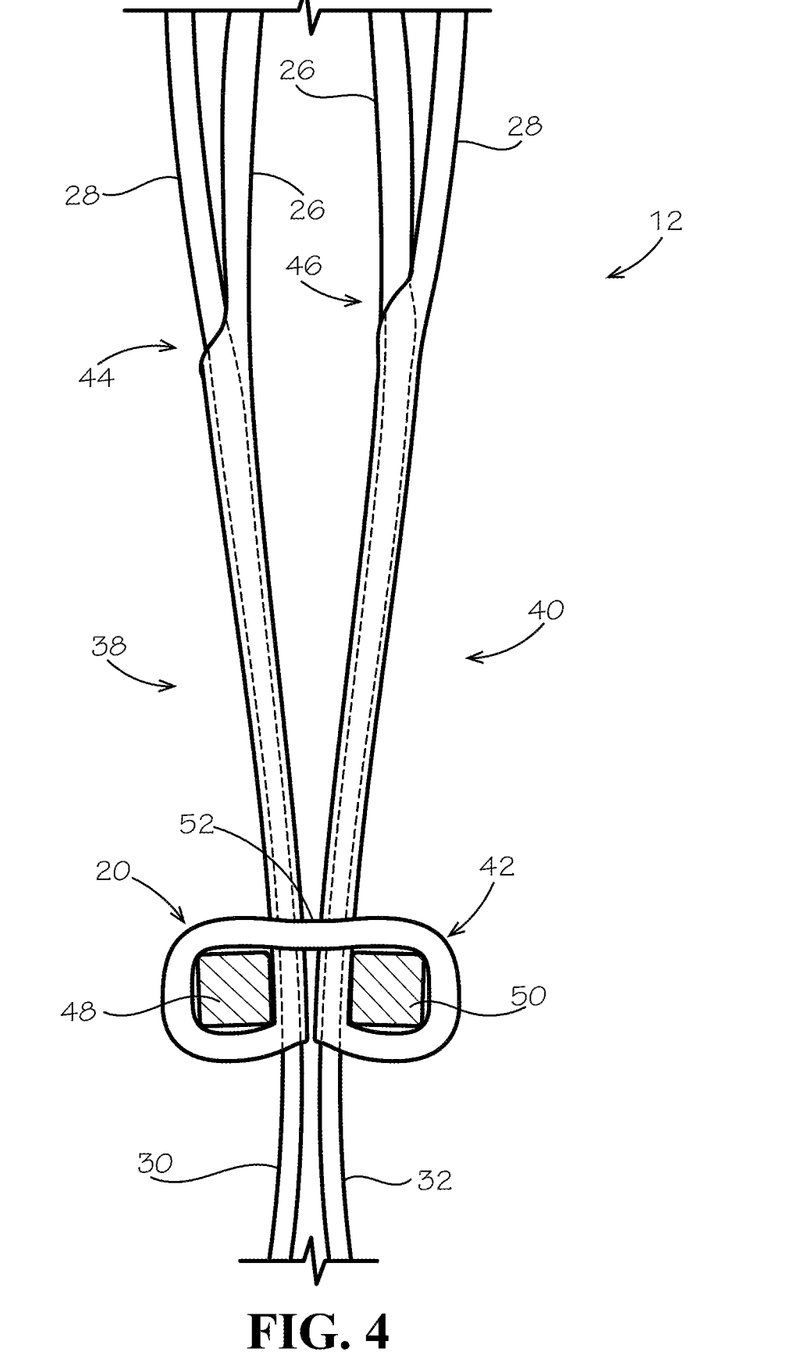
FIG. 4 illustrates a detail perspective view of the suture construct of FIG. 3.

Referring further to FIGS. 2-4, suture 12 includes an adjustable main loop 24 comprising a first strand 26 and a second strand 28. First and second strands 26, 28 are portions of a single suture forming a double loop. Each of first and second strands 26, 28 passes through the fixed pulley loop 22. During use, pulley loop 22 is fixed in place inside femoral tunnel 36, and pulley loop 22 operates as an anchor around which first and second strands 26, 28 may slide when main loop 24 is tightened.

As shown in FIG. 3, main loop 24 includes a first self-cinching sleeve 38 and a second self-cinching sleeve 40 positioned substantially parallel to the first self-cinching sleeve 38. First self-cinching sleeve 38 is formed on first strand 26, and second strand 28 enters a first sleeve opening 44 on first strand 26. Second strand 28 passes through the interior hollow core of first strand 26 toward spring button 20. Second strand 28 exits the sleeve at or near the spring button 20, forming first tag end 30. During use, first tag end 30 may be pulled, causing second strand 28 to slide inside the hollow interior core of first strand 26 inside first self-cinching sleeve 38. When tension is applied, the first self-cinching sleeve 38 clamps down on second strand 28, thereby locking first and second strands in a fixed axial position relative to each other inside first self-cinching sleeve 38. As more tension is applied the clamping force increases. Such a configuration allows the spring button 20 to be pulled tight against the distal end of spring 18 to tighten the repair device 10.

Similarly, second self-cinching sleeve 40 is formed on second strand 28, and first strand 26 enters a second sleeve opening 46 on second strand 28. First strand 26 passes through the interior hollow core of second strand 28 toward spring button 20. First strand 26 exits the sleeve at or near the spring button 20, forming second tag end 32. During use, second tag end 32 may be pulled, causing first strand 26 to slide inside the hollow interior core of second strand 28 inside second self-cinching sleeve 40. When tension is applied, the second self-cinching sleeve 40 clamps down on first strand 26, thereby locking first and second strands in a fixed axial position relative to each other inside second self-cinching sleeve 40. As more tension is applied the clamping force increases. Such a configuration allows the spring button 20 to be pulled tight against the distal end of spring 18 to tighten the repair device 10.

In some embodiments, first and second tag ends 30, 32 are both pulled simultaneously to tighten main loop 24 to a desired length and tension. As shown in FIG. 4, main loop 24 is formed when the suture material is attached to the spring button 20. In some embodiments, spring button 20 includes a first bar 48 and a second bar 50. The suture material forms a hitch 42 around the first and second bars 48, 50 as shown in FIG. 4. In some embodiments, a cross strand 52 spans the first and second bars 48, 50 on the inner side of the spring button 20. The first self-cinching sleeve 38 along with the interior second strand 28 both pass alongside cross strand 52 in some embodiments. In other embodiments, the first self-cinching sleeve 38 along with the interior second strand 28 puncture and pass transversely through the suture material of the cross strand 52. Similarly, the second self-cinching sleeve 40 along with the interior first strand 26 both pass alongside cross strand 52 in some embodiments. In other embodiments, the second self-cinching sleeve 40 along with the interior first strand 26 puncture and pass transversely through the suture material of the cross strand 52.

Figure 5:
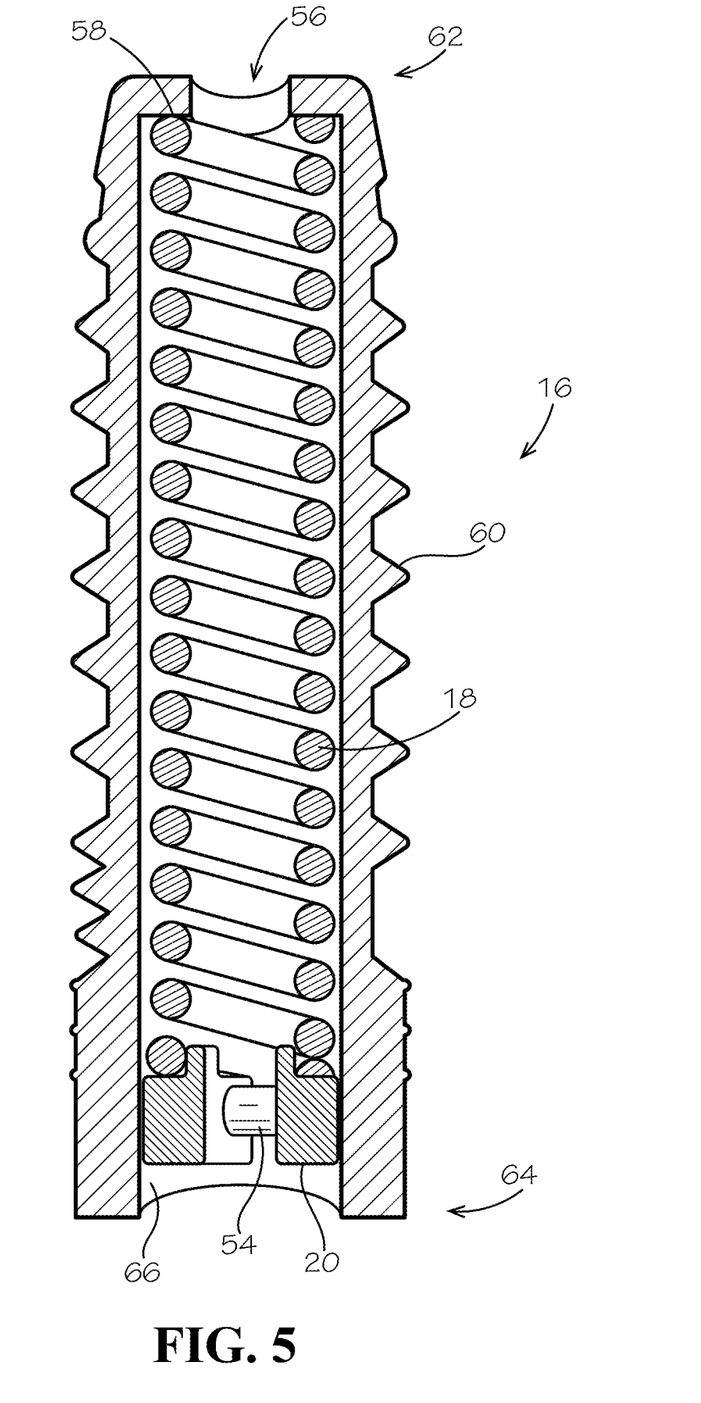
FIG. 5 illustrates a cross-sectional perspective view of an embodiment of a dynamic ligament repair device in accordance with the present disclosure.

Referring to FIG. 5, in some embodiments a screw 16 includes a tube shape including a hollow interior bore. Screw 16 includes external threads 60, and an interior surface 66. A compression spring 18 is disposed inside the interior bore of the screw 16. Screw 16 includes a proximal end 62 configured to be inserted into a drill tunnel in a bone such as a tibia or femur, and a distal end 64 configured to be the trailing end of the screw 16 as it is inserted into a drill tunnel. A spring button 20 is positioned inside the bore of screw 16 adjacent to the distal end of the spring 18 in some embodiments. Spring button 20 is configured to provide a moveable anchor for a suture construct 12 extending through proximal opening 56 on screw 16 and into the interior bore as shown in FIG. 1. One or more bridges 54 span across spring button 20 to provide attachment locations for one or more sutures.

During use, spring 18 is compressed to a length shorter than the overall length of screw 16 inside the interior bore. End wall 58 extends radially inwardly into the bore adjacent proximal opening 56 to retain spring 18 during compression. As a patient's joint flexes through a range of motion, the spring button 20 presses against the distal end of spring 18 and translates inside the hollow bore of screw 16 when tension is applied via suture 12.

Figure 6:
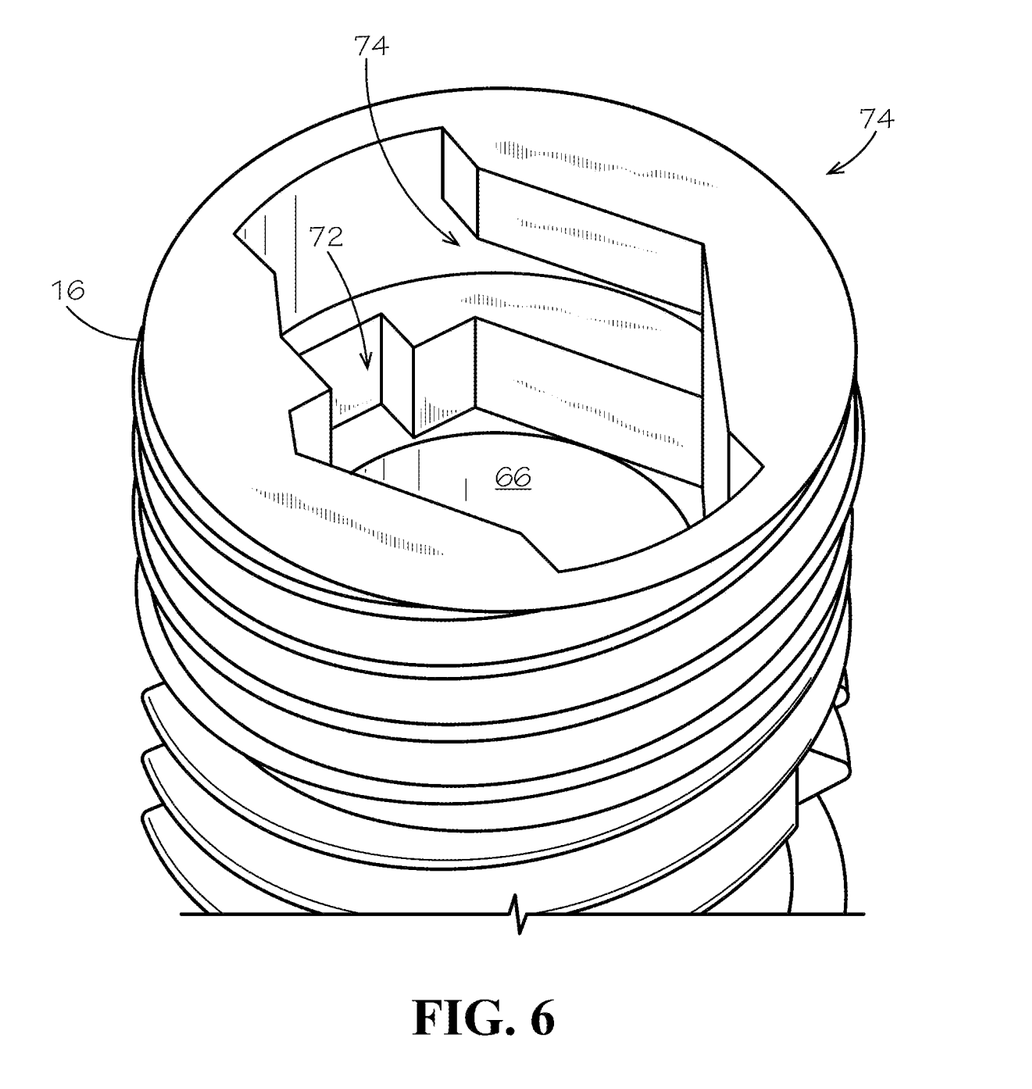
FIG. 6 illustrates a partial perspective view of an embodiment of a threaded screw implant for use with a dynamic ligament repair device in accordance with the present disclosure.

During a surgical procedure, screw 16 is placed into a drill tunnel in a patient's bone. The spring 18 may then be pre-loaded to a desired compression at an intermediate compression length that is less than the fully uncompressed length of the spring, but greater than the fully compressed length of the spring. The initial pre-load placed on the compression spring 18 corresponds to a desired initial tensile force load on suture 12. The initial pre-load is applied to spring 18 using a manual spring compression tool, as shown in Exhibit 1. Referring to FIG. 6, the distal end 64 of screw 16 is shown in some embodiments.

The distal end 64 of screw 16 includes a unique geometry in some embodiments including several features. In some embodiments, distal end 64 includes a compression tool socket 74 configured for receiving a portion of a compression tool in a locking engagement to provide a pre-load on compression spring 18, as described in Exhibit 1.

The distal end 64 of screw 16 also includes a driver socket 72 configured to receive a keyed driver inserted in the socket to turn screw 16 relative to bone for driving the screw 16 into a drill tunnel.

Following installation of screw 16 into a drill tunnel, pre-loading of compression spring 16 using the manual compression tool, and tightening of the adjustable main loop on suture construct 12 via first and second self-cinching sleeves by pulling on first and second tag ends, the compression tool may be removed and an end cap may be inserted into the opening on distal end 64 of spring 16.

End cap includes first and second openings in some embodiments to facilitate passage of one or more strands of suture construct 12. End cap also includes first and second locking flanges that engage cap socket 74 via angular rotation. When end cap is inserted into the opening at the distal end of the screw, a resilient flange biases the end cap in rotation such that a locking flange engages the cap socket 74. Additional features of the end cap are disclosed in Exhibit 1 attached hereto.

Figure 7:
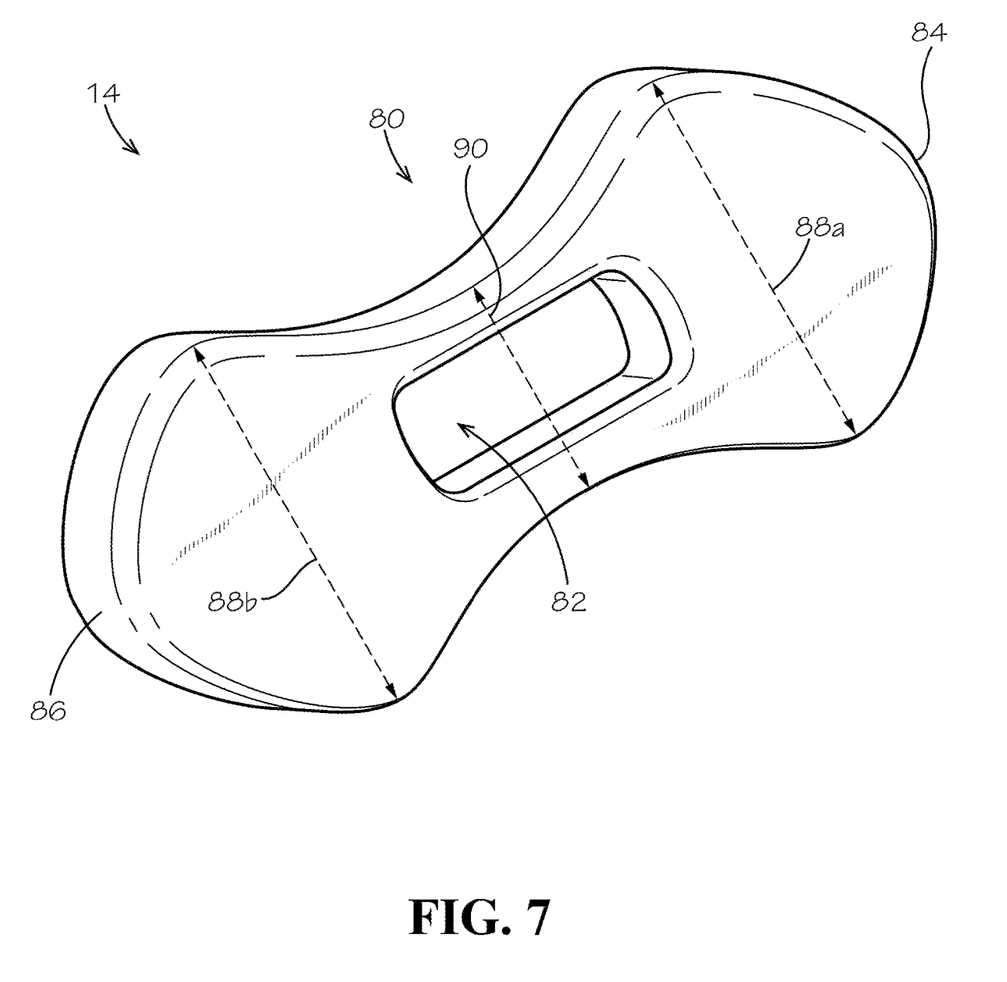
FIG. 7 illustrates a perspective view of an embodiment of a suture anchor for use with a dynamic ligament repair device in accordance with the present disclosure.

Referring to FIG. 7, an embodiment of a femoral side suture anchor 14 is shown. The anchor includes a suture button 80 having a central opening 82 shaped to accommodate a suture material. In some embodiments, fixed loop 22 is passed through a drill tunnel on the femur and is inserted through central opening 82 and the passed loop is wrapped around first end 84 or second end 86 to form a girth hitch around suture button 80. At that point, adjustable main loop 24 is tightened by pulling on first and second tag ends 30, 32, thereby pulling suture button 80 against the femoral cortex. As such, suture button 80 provides a fixed anchor point for pulling against to tighten suture construct 12.

Suture button 80 includes a first tapered end 84 forming a point and having a first end width 88a greater than midsection width 90. Similarly, suture button 80 includes a second tapered end 86 forming a point and having a second end width 88b greater than midsection width 90. In some embodiments, first end width 88a and second end width 88b are substantially equal.

Additionally, in some embodiments, suture button 80 also provides an anchor point for tightening a ligament suture stitched onto the ligament undergoing repair, such as an ACL. In some embodiments, the ACS is stitched using a conventional suture stitched into the ligament tissue during the operation. The ligament suture is then passed through the same drill tunnel on the femur through which suture construct 12 extends. The ligament suture may be tied directly onto the suture button 80 to secure the ligament in place against the femur. During flexion and extension of the joint, the ligament suture does not bear the majority of the tensile load because the suture construct 12, when fully tightened, operates as tensile stent to maintain proper orientation of the joint and to relieve stress and strain on the repaired ligament. Additionally, the dynamic motion of the spring button translating inside the housing against the compression spring during motion of the joint absorbs energy that would otherwise adversely affect the repair of the ligament.

Numerous other features of the present disclosure are discussed in Exhibit 1 attached hereto, all of which is hereby incorporated by reference in its entirety.

What is claimed is:

1. A dynamic ligament repair apparatus, comprising:
   a suture construct including an adjustable main loop;
   a screw defining a hollow interior bore;
   a compression spring disposed in the bore of the screw;
   a spring button disposed in the hollow interior bore proximate the distal end of the spring, the spring button including a first bar and a second, wherein the suture construct engages the first and second bars of the spring button and a cross strand spanning the first and second bars, forming a hitch around the first and second bars;
   wherein the spring button is configured to translate inside the bore and compress the spring when tension is applied to the suture construct.

2. The apparatus of claim 1, further comprising:
   first and second self-cinching sleeves disposed on the adjustable main loop of the suture construct.

3. The apparatus of claim 2, further comprising:
   a fixed loop disposed on the adjustable main loop of the suture construct.

4. The apparatus of claim 3, further comprising:
   a suture anchor engaging the fixed loop, wherein the fixed loop forms a pulley for tightening the adjustable main loop.

5. A dynamic ligament repair apparatus, comprising:
   a housing including a threaded exterior and a hollow interior bore, the housing including a proximal end configured to be oriented toward a ligament and a distal end configured to be oriented away from the ligament, the housing including an end wall defining an opening at the proximal end;
   a compression spring disposed in the interior bore, the spring having a proximal spring end retained by the proximal end wall inside the interior bore and a distal spring end configured to be oriented away from the ligament;
   a spring button disposed inside the bore at the distal spring end, the spring button including a first bar and a second, wherein the spring button is moveable along a longitudinal axis of the housing inside the interior bore; and
   an end cap disposed on the distal end of the housing.

6. The apparatus of claim 5, further comprising:
   a suture construct including an adjustable main loop including first and second self-cinching sleeves, wherein the suture construct is secured to the one or more bars of the spring button.

7. The apparatus of claim 6, wherein the suture construct extends from the spring button through an interior passage along a centerline of the compression spring and through the opening at the end wall of the housing.

8. The apparatus of claim 7, wherein the suture construct is configured to pull the spring button toward the spring and compress the spring during use.

9. The apparatus of claim 8, wherein the spring does not extend beyond the distal end of the housing.

10. The apparatus of claim 9, further comprising a suture anchor disposed on the suture construct opposite the housing.

11. The apparatus of claim 10, wherein the suture anchor is a button.

12. The apparatus of claim 11, further comprising an end cap driver configured to install the end cap on the housing.

13. A dynamic ligament repair apparatus, comprising:
a femoral side suture anchor;
a screw implant having a threaded exterior surface and defining an interior axial bore, the implant including a proximal end configured to be oriented toward a ligament and a distal end configured to be oriented away from the ligament;
a proximal opening defined in the screw implant at the proximal end;
a coiled compression spring housed inside the axial bore in the threaded screw implant, the spring having a proximal spring end configured to be oriented toward the ligament and a distal spring end configured to be oriented away from the ligament, the spring defining an inner spring passage;
an end wall on the screw implant extending radially inwardly into the axial bore adjacent the proximal opening, the end wall configured to retain the spring during compression;
a moveable spring button positioned inside the axial bore adjacent the distal spring end, the spring button including a first bar and a second; and
a suture extending between the first bar and the second bar of the spring button and the suture anchor, wherein the suture passes through the inner spring passage, through a cross strand spanning the first and second bars, and out the proximal opening in the screw implant.

14. The apparatus of claim 13, wherein when the suture is pulled toward the ligament, the suture button travels toward the ligament and compresses the compression spring inside the axial bore.

15. The apparatus of claim 14, wherein when the suture is released away from the ligament, the suture button travels away from the ligament and allows the compression spring to extend inside the axial bore.

16. The apparatus of claim 15, further comprising a bridge disposed on the suture button, wherein the suture engages the bridge.

17. The apparatus of claim 16, wherein the spring is entirely housed within the axial bore of the screw implant.

18. The apparatus of claim 17, wherein the spring does not extend beyond the distal end of the screw implant.

19. The apparatus of claim 13, wherein when the suture extends through the cross strand, a hitch is formed around the first and second bars.

* * * * *